(12) United States Patent
Grimaldi et al.

(10) Patent No.: US 7,439,384 B2
(45) Date of Patent: Oct. 21, 2008

(54) PEROXYESTER PREPARATION METHOD

(75) Inventors: Sandra Grimaldi, Sainte Foy les-Lyon (FR); Gurusamy Jeyaraj, Cuddalore (IN)

(73) Assignee: ATOFINA, Puteaux (FR)

( * ) Notice: Subject to any disclaimer, the term of this patent is extended or adjusted under 35 U.S.C. 154(b) by 189 days.

(21) Appl. No.: 10/467,782

(22) PCT Filed: Feb. 7, 2002

(86) PCT No.: PCT/FR02/00475

§ 371 (c)(1),
(2), (4) Date: Apr. 16, 2004

(87) PCT Pub. No.: WO02/064555

PCT Pub. Date: Aug. 22, 2002

(65) Prior Publication Data

US 2004/0176632 A1 Sep. 9, 2004

(30) Foreign Application Priority Data

Feb. 13, 2001 (FR) .................................. 01 01921

(51) Int. Cl.
*C07C 67/02* (2006.01)
*C07C 69/02* (2006.01)
(52) U.S. Cl. ...................................... 560/252; 560/231
(58) Field of Classification Search ................ 560/302, 560/129, 205, 231
See application file for complete search history.

(56) References Cited

U.S. PATENT DOCUMENTS

| 3,435,060 A | 3/1969 | Johannes et al. |
| 4,525,308 A * | 6/1985 | Sanchez ..................... 560/302 |
| 4,634,753 A | 1/1987 | Sanchez |
| 2004/0049070 A1* | 3/2004 | Overkamp et al. ............. 562/4 |

FOREIGN PATENT DOCUMENTS

| EP | 0126216 | 11/1984 |
| GB | 1106953 | 3/1968 |

OTHER PUBLICATIONS

Chemical Abstracts, vol. 99, No. 20, Nov. 14, 1983, Columbus, Ohio, US ; Abstract No. 159030, Horia, Mihai et al: "Tert-Butyl per-2-ethylhexanoate," XP002180202.
Database WPI Section Ch, Week 198518 Derwent Publications Ltd., London, GB; AN 1985-107394, XP002180203.

* cited by examiner

*Primary Examiner*—Karl J Puttlitz
(74) *Attorney, Agent, or Firm*—Millen, White, Zelano & Branigan, P.C.

(57) ABSTRACT

The present invention relates to a process for the preparation of a peroxyester which can be used in particular in polymerizations, such as the polymerization of vinyl chloride, or in the thermosetting of polyester resins.

This process comprises the reaction of a hydroxyhydroperoxide salt with an acid halide or an acid anhydride under the following conditions:
 the molar ratio $R_b$ of the hydroxyhydroperoxide corresponding to the hydroxyhydroperoxide salt to the acid halide is between 0.5 and 1.5; or alternatively the molar ratio $R_b'$ of the hydroxyhydroperoxide corresponding to the hydroxyhydroperoxide salt to the acid anhydride is between 1.0 and 3.0;
 the hydroxyhydroperoxide salt was prepared beforehand by reaction of the corresponding hydroxyhydroperoxide with a base according to a molar ratio $R_a$ of the base to the hydroxyhydroperoxide of between 0.5 and 1.5; and this process is carried out in aqueous media.

The invention also relates to an aqueous emulsion comprising the peroxyester obtained and to a polymerization process employing a radical initiator comprising this peroxyester.

22 Claims, No Drawings

PEROXYESTER PREPARATION METHOD

The present invention relates to a process for the preparation of a peroxyester which can be used in particular in polymerizations, such as the polymerization of vinyl chloride, or in the thermosetting of polyester resins.

Numerous documents of the prior art mention the preparation of peroxyesters:

European Patent Application No. 667 339, which relates to unsaturated peroxides and to polymers obtained using these peroxides;

European Patent Application No. 126 216, which relates to hydroxy-t-alkyl peroxyesters having 10-hour half-life temperatures of less than 75° C.;

U.S. Pat. No. 3,624,124, which relates to tertiary hydroperoxide and tertiary alkyl peresters;

European Patent Application No. 381 135, which discloses hydroxyperoxides having 10-hour half-life temperatures of between 85 and 100° C.; and European Patent Application No. 474 227, which relates to functionalized peroxides intended for polymerization reactions.

However, in all these documents, the peroxyesters are prepared in the presence of a solvent and sometimes of a phase transfer catalyst.

During the preparation of peroxyesters having a hydroxyl group in the γ position with respect to the O—O peroxide functional group, problems of decanting, that is to say of poor separation of the organic phase and of the aqueous phase, may be encountered.

To overcome these problems, use is then made of a solvent which makes it possible to accelerate the phenomenon of decanting; however, this solvent poses an additional problem: part of it remains in the peroxyester, which is a nuisance during the use of the peroxyester because of the subsequent presence of solvent in the polymer.

Another solution consists in patiently waiting for the decanting to take place unaided, which can take several days.

It has now been discovered that it is possible to obtain rapid decanting without having recourse to a solvent.

A subject-matter of the invention is therefore a process for the preparation of a peroxyester comprising the reaction of a hydroxyhydroperoxide salt with an acid halide or an acid anhydride, in which:

the molar ratio $R_b$ of the hydroxyhydroperoxide corresponding to the hydroxyhydroperoxide salt to the acid halide is between 0.5 and 1.5; or alternatively the molar ratio $R_b'$ of the hydroxyhydroperoxide corresponding to the hydroxyhydroperoxide salt to the acid anhydride is between 1.0 and 3.0;

the hydroxyhydroperoxide salt was prepared beforehand by reaction of the corresponding hydroxyhydroperoxide with a base according to a molar ratio $R_a$ of the base to the hydroxyhydroperoxide of between 0.5 and 1.5; and this process is carried out in aqueous media.

Such a process therefore offers the following advantages:

the reaction of the hydroperoxide salt with the acid halide or anhydride can now be carried out in the absence of organic solvent and, if appropriate, of phase transfer catalyst;

the decanting takes place rapidly, which, first, makes possible a saving in time and, secondly, avoids the need to store certain rather unstable peroxyesters in low-temperature storage areas;

the peroxyester obtained is devoid of any solvent; any subsequent stage of evaporation or distillation of the solvent is thus avoided, which improves the yield;

the purity of the peroxyester obtained is satisfactory;

the absence of solvent additionally eliminates the risk of introducing, into the peroxyester or the final product, possible impurities present in the solvent;

the peroxyester can be used as obtained, that is to say without subsequent purification, without the occurrence, for example, during use in polymerization reactions, of side reactions, such as transfer reactions, or problems of colour or smell of the polymer obtained.

Another subject-matter of the invention is an aqueous emulsion comprising at least one peroxyester obtained by the process according to the invention.

Another subject-matter of the invention is a polymerization process employing a radical initiator comprising at least one peroxyester obtained by the process according to the invention.

Other characteristics and advantages of the invention will become apparent on reading the description which follows and which is illustrated by examples.

DETAILED DESCRIPTION OF THE INVENTION

The preparation process according to the invention can therefore be carried out in the aqueous phase.

It can comprise a preliminary stage of preparation of the hydroperoxide salt by reaction of a hydroperoxide with a base.

Thus, the synthesis of the peroxyester can be illustrated by the following reaction scheme:

Stage a):

ROOH+base→ROOM

Stage b):

R'C(O)X or (R'CO)$_2$O+ROOM→R'—C(O)—O—O—R in which:

ROOH is a hydroperoxide;

ROOM is a salt of the hydroperoxide;

R'C(O)X is an acid halide;

(R'CO)$_2$O is an acid anhydride.

One advantage of the process according to the invention is that stage b) can be carried out in the reactor which has been used to carry out stage a).

Stage a)

The starting hydroperoxide ROOH can be any hydroperoxide. It is preferably a hydroxyhydroperoxide.

Use is in particular made, as hydroxyhydroperoxides, of those in which the hydroxyl group is situated in the 3 position with respect to the hydroperoxy group.

In addition, it is preferable to use hydroxy(tertiary-alkyl) hydroperoxides.

Mention may be made, as examples of such compounds, of those corresponding to the following general formula:

HO—C(R$_3$)(R$_4$)—CH$_2$—C(R$_1$)(R$_2$)—OOH in which:

R$_1$ and R$_2$ are, independently of one another, an alkyl having from 1 to 4 carbon atoms;

R$_3$ and R$_4$ are, independently of one another, a hydrogen or an alkyl having from 1 to 4 carbon atoms;

R$_1$ and R$_3$ can be connected to one another via an alkylene bridge having 3 carbon atoms, this bridge optionally being substituted by an alkyl having from 1 to 4 carbon atoms; and R$_3$ can additionally be a —CH$_2$—C(R$_1$)(R$_2$)—OOH group, R$_1$ and R$_2$ being as defined above.

Mention may be made, as hydroxy(t-alkyl) hydroperoxides, of 3-hydroxy-1,1-dimethylpropyl, 3-hydroxy-1,1-dimethylbutyl, 1-ethyl-3-hydroxy-1-methylpentyl, 1,1-diethyl-3-hydroxybutyl and 5-hydroxy-1,3,3-trimethylcyclohexyl hydroperoxides.

According to the invention, the preferred hydroxyhydroperoxides are hexylene glycol hydroperoxides, in particular 3-hydroxy-1,1-dimethylbutyl hydroperoxide.

These hydroxy(t-alkyl) hydroperoxides can be prepared by treating the corresponding hydroxy (t-alcohols) with an excess of hydrogen peroxide in the presence of a highly acidic catalyst, such as sulphuric acid, phosphoric acid, perchloric acid or p-toluenesulphonic acid.

For example, hexylene glycol hydroperoxide can be prepared in this way from commercial hexylene glycol according to the teachings of U.S. Pat. No. 336,872.

The hydroxy(t-alcohols) can in their turn be prepared in a known way.

Use may be made, as base for stage a) of the process, of inorganic bases, such as NaOH, KOH, LiOH, $Na_2CO_3$, $K_2CO_3$, $NaHCO_3$, $KHCO_3$, $Ca(OH)_2$, $Ba(OH)_2$, $CaCO_3$ or $Na_3PO_4$, or alternatively of organic bases, such as amines, for example pyridine, N,N-dimethylaniline, 4-(N,N-dimethylamino)pyridine, triethylamine, tributylamine, 1azabicyclo[2.2.2]octane, 1,4-diazabicyclo[2.2.2]octane, 1,8-diazabicyclo[5.3.0]undec-7-ene, urea and tetramethyl-urea.

Use is preferably made of a base, in particular potassium hydroxide or sodium hydroxide. Potassium hydroxide is the preferred base.

The molar ratio $R_a$ of the base to the hydroperoxide is generally between 0.5 and 1.5.

According to another advantageous embodiment of the invention, the molar ratio $R_a$ is between 0.9 and 1.3, preferably between 1.00 and 1.22 and in particular between 1.10 and 1.19.

Stage a) is generally carried out at a temperature of 20-25° C., the hydroxyhydroperoxide generally being reacted as is (in the substantially pure state and without prior dissolution in an organic solvent), gradually, with stirring, with the organic base, the latter optionally being in the form of an aqueous solution.

The reaction mixture is then generally kept stirred for a few minutes in order to bring the formation of the hydroxyhydroperoxide salt to completion.

Stage b)

This stage is carried out between the hydroperoxide salt obtained on completion of stage a) and either an acid anhydride or an acid halide.

The acid anhydride can be chosen from the group consisting of the anhydrides of 2-methoxypropionic, isobutyric, tert-butyric, pivalic, 2,2-dimethylbutyric, 2-ethylbutyric, hexanoic, neohexanoic, benzoic, heptanoic, neoheptanoic, 2-ethylhexanoic, octanoic, neooctanoic, 2-phenoxypropanoic, 2-phenylpropanoic, nonanoic, isononanoic, neononanoic, 2-methyl-2-phenylpropionic, 2-phenylbutyric, decanoic, neodecanoic, dodecanoic, 2-butyloctanoic, neododecanoic, undecanoic, neotridecanoic, methacrylic, methylcrotonic and 2-methyl-2-butenoic acids.

According to a preferred embodiment of the invention, stage b) is carried out with an acid halide.

This acid halide generally has, as empirical formula, the formula R'COX, in which:

R' corresponds to one of the following formulae:

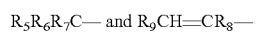

in which:

$R_5$ is a hydrogen or an alkyl having from 1 to 8 carbon atoms;

$R_6$ is an alkyl having from 1 to 8 carbon atoms;

$R_7$ is an alkyl having from 1 to 8 carbon atoms, an alkenyl having from 2 to 8 carbon atoms, an aryl having from 6 to 10 carbon atoms, an alkoxy having from 1 to 6 carbon atoms or an aryloxy having from 6 to 10 carbon atoms;

$R_8$ and $R_9$ are, independently of one another, an alkyl having from 1 to 4 carbon atoms; and X is a halogen.

Use may thus be made, as acid halides, of 2-methoxypropionyl, isobutyroyl, tert-butyroyl, pivaloyl, 2,2-dimethylbutyroyl, 2-ethylbutyroyl, hexanoyl, neohexanoyl, benzoyl, heptanoyl, neoheptanoyl, 2-ethyl-hexanoyl, octanoyle, neooctanoyl, 2-phenoxypropanoyl, 2-phenylpropanoyl, nonanoyl, isononanoyl, neononanoyl, 2-methyl-2-phenylpropionyl, 2-phenylbutyroyl, decanoyl, neodecanoyl, dodecanoyl, 2-butyloctanoyl, neododecanoyl, undecanoyl, neotridecanoyl, methacryloyl, methylcrotonoyl and 2-methyl-2-butenoyl halides.

Preferably, the halogen X is a chlorine atom.

According to the invention, the most advantageous acid halide is neodecanoyl chloride with the empirical formula $t\text{-}C_9H_{19}\text{—COCl}$.

The acid chlorides can be prepared in a known way, for example from the corresponding acids, by reaction with chlorinating agents, such as $PCl_3$, $POCl_3$, $PCl_5$, $SOCl_2$, phosgene (in the presence of N,N-dimethylformamide) or trichlorobenzene, and then by separation of the acid chloride from the reaction medium.

According to an advantageous embodiment of the invention, the molar ratio $R_b$ of the hydroperoxide (corresponding to the hydroperoxide salt) to the acid halide is between 0.9 and 1.2, preferably between 1.00 and 1.17 and in particular between 1.10 and 1.16.

In stage b), the acid anhydride or halide can be added as is (that is to say, without prior dissolution in an organic solvent) to the salt obtained on completion of stage a), for example over 5 to 60 minutes, preferably over 10 to 20 minutes, and generally with stirring. The temperature of the beginning of addition is from 15 to 25° C. and preferably from 18 to 23° C.

The addition is generally fairly exothermic and there is generally a change from a temperature of 20° C. to 30° C. Subsequently, the reaction temperature is generally maintained between 20 and 40° C. and preferably between 25 and 35° C. Such ranges of reaction temperatures are generally sufficient to produce good reaction kinetics without causing the peroxyester formed to decompose. The reaction time is generally from 10 to 90 minutes and preferably from 20 to 40 minutes.

The reaction medium is subsequently treated generally at ambient temperature.

Various additional stages can be implemented.

A first washing with water is carried out and the aqueous phase is separated from the organic phase and is then removed from the medium. Another washing with a 3% aqueous potassium hydroxide (or sodium hydroxide) solution is carried out and the aqueous phase is separated from the organic phase and is then removed from the medium.

A phase transfer catalyst can optionally be used to facilitate the separation of the phases.

The peroxyester, which is the predominant constituent of the organic phase, is thus obtained.

The organic phase can subsequently be quantitatively determined by an iodometric method to determine the peroxyester content. The water content can also be approximately measured by addition of heptane to the organic phase and then more accurately by a Karl-Fischer method.

Uses

Peroxyesters and in particular 1,1-dimethyl-3-hydroxybutyl peroxyneodecanoate have numerous applications in industry.

They can participate, in particular, in polymerization reactions, for example in the polymerization of vinyl chloride, or in the thermosetting of polyester resins.

Reference may be made to the following documents to find examples of applications of peroxyesters:

International Application No. WO 99/31194, which relates to the polymerization of vinyl monomers;
U.S. Pat. No. 5,612,426, which relates to the production of PVC;
Japanese Patent Application No. JP 7258316, which relates to the suspension polymerization of vinyl chloride;
Japanese Patent Application No. JP 7258315, which relates to the preparation of an aqueous emulsion; and
Japanese Patent Applications Nos. JP 7252308 and JP 7252307, which disclose the preparation of PVC.

EXAMPLES

The following examples illustrate the present invention without, however, limiting the scope thereof.

They describe the synthesis of 1,1-dimethyl-3-hydroxybutyl peroxyneodecanoate.

Example 1

A 250 ml jacketed reactor, equipped with a mechanical stirrer and a thermometer and connected to an automatically-controlled heating/cooling system, is charged with 62.42 g of a 23% aqueous KOH solution.

37.96 g of hexylene glycol hydroperoxide, with a purity of 78%, are gradually added while maintaining the temperature of the reactor at 20° C. The mixture is subsequently stirred for two minutes at 20° C. at a stirring rate of 200 revolutions per minute.

36.94 g of neodecanoyl chloride, with a purity of 99.9%, are then added to the reactor while stirring at 250 revolutions per minute. The temperature changes from 20° C. at the beginning of the addition to 26.9° C. at the end of the addition.

The automatically-controlled heating/cooling system is subsequently adjusted to 30° C. and the reaction mass is stirred for 30 minutes at 30° C. at a stirring rate of 250 revolutions per minute.

The automatically-controlled heating/cooling system is then adjusted to 20° C., 24.7 g of water are added and the reaction medium is left standing for 5 minutes, which makes it possible to remove the aqueous phase from the medium. The medium is subsequently washed with 64.6 g of a 3% aqueous KOH solution at a stirring rate of 280 revolutions per minute for 5 minutes.

After separating the phases and removing the aqueous phase, 49.1 g of an organic phase are obtained.

An iodometric analysis makes it possible to measure a peroxyester purity of 91.4%; the product comprises approximately 2.1% of water, which leads to a product purity of 93.3% (water not being regarded as an impurity). The yield, based on neodecanoyl chloride, is 82.3%.

Example 2

A 250 ml jacketed reactor, equipped with a mechanical stirrer and a thermometer and connected to an automatically-controlled heating/cooling system, is charged with 62.40 g of a 23% aqueous KOH solution.

38.28 g of hexylene glycol hydroperoxide, with a purity of 75%, are gradually added while maintaining the temperature of the reactor at 20° C. The mixture is subsequently stirred for two minutes at 20° C. at a stirring rate of 200 revolutions per minute.

36.93 g of neodecanoyl chloride, with a purity of 95.5%, are then added to the reactor while stirring at 250 revolutions per minute. The temperature changes from 20° C. at the beginning of the addition to 30.3° C. at the end of the addition.

The automatically-controlled heating/cooling system is subsequently adjusted to 30° C. and the reaction mass is stirred for 30 minutes at 30° C. at a stirring rate of 250 revolutions per minute.

Treatment is then carried out with 2 g of 50% hydrogen peroxide and the reaction medium is stirred at 30° C. for 15 minutes.

The automatically-controlled heating/cooling system is subsequently adjusted to 20° C., 24.4 g of water are added and the reaction medium is left standing for 5 minutes, which makes it possible to remove the aqueous phase from the medium. The medium is subsequently washed with 64.9 g of a 3% aqueous KOH solution at a stirring rate of 280 revolutions per minute for 5 minutes.

After separating the phases and removing the aqueous phase, 44.9 g of an organic phase are obtained.

An iodometric analysis makes it possible to measure a peroxyester purity of 78.2%; the product comprises approximately 8.9% of water, which leads to a product purity of 85.9% (water not being regarded as an impurity). The yield, based on neodecanoyl chloride, is 72.2%.

Example 3 (Comparative)

A 250 ml jacketed reactor, equipped with a mechanical stirrer and a thermometer and connected to an automatically-controlled heating/cooling system, is charged with 65 g of a 30% aqueous KOH solution.

36.88 g of hexylene glycol hydroperoxide, with a purity of 78%, are gradually added while maintaining the temperature of the reactor at 20° C. The mixture is subsequently stirred for two minutes at 20° C. at a stirring rate of 200 revolutions per minute.

36.94 g of neodecanoyl chloride, with a purity of 99.9%, are then added to the reactor while stirring at 250 revolutions per minute. The temperature changes from 20° C. at the beginning of the addition to 28° C. at the end of the addition.

The automatically-controlled heating/cooling system is subsequently adjusted to 30° C. and the reaction mass is stirred for 30 minutes at 30° C. at a stirring rate of 250 revolutions per minute.

The automatically-controlled heating/cooling system is subsequently adjusted to 20° C., 24.5 g of water are added and the reaction medium is left standing for 5 minutes, which makes it possible to remove the aqueous phase from the medium. The medium is subsequently washed with 64.6 g of a 3% aqueous KOH solution at a stirring rate of 280 revolutions per minute for 5 minutes.

No separation of the phases is observed.

The invention claimed is:

1. A process for the preparation of a peroxyester said process comprising conducting the following sequential steps:
   (a) reacting an hydroxyhydroperoxide with a base in the absence of an organic solvent, and with a molar ratio $R_a$ of the base to the hydroperoxide of between 0.9 and 1.3, to obtain a salt of the hydroxyhydroperoxide,
   (b) on completion of step (a) reacting resultant salt of hydroxyhydroperoxide with an acid chloride or an acid anhydride in the absence of an organic solvent to form a peroxyester, wherein the mol ratio $R_b$ of the hydroxyhydroperoxide corresponding to the salt to the acid halide is between 0.5 and 1.5 or the mol ratio $R_b$ of the hydroxyhydroperoxide corresponding to the hydroxyhydroperoxide salt to the acid anhydride is between 1.0 and 3.0, (c) recovering said peroxyester from step (b) so as to produce a final product, said recovery being conducted in the absence of an organic solvent, and wherein the hydroxyhydroperoxide is a hydroxy(tertiary-alkyl) hydroperoxide in which the hydroxyl group is situated in the 3 position with respect to the hydroperoxy group.

2. A process according to claim 1 wherein the mol ratio $R_a$ is between 1.0 and 1.22.

3. A process according to claim 1 wherein the mol ratio $R_a$ is between 1.10 and 1.19.

4. A process for the preparation of a peroxyester said process comprising conducting the following sequential steps:

(a) reacting an hydroxyhydroperoxide with a base in the absence of an organic solvent, and with a molar ratio $R_a$ of the base to the hydroperoxide of between 0.9 and 1.3, to obtain a salt of the hydroxyhydroperoxide, (b) on completion of step (a) reacting resultant salt of hydroxyhydroperoxide with an acid chloride or an acid anhydride in the absence of an organic solvent to form a peroxyester, wherein the mol ratio $R_b$ of the hydroxyhydroperoxide corresponding to the salt to the acid halide is between 1.00 and 1.17 or the mol ratio $R_b$ of the hydroxyhydroperoxide corresponding to the hydroxyhydroperoxide salt to the acid anhydride is between 1.00 and 1.17, (c) recovering said peroxyester from step (b) so as to produce a final product, said recovery being conducted in the absence of an organic solvent, and wherein the hydroxyhydroperoxide is a hydroxy(tertiary-alkyl) hydroperoxide in which the hydroxyl group is situated in the 3 position with respect to the hydroperoxy group.

5. A process according to claim 1 wherein said recovery in the absence of an organic solvent comprises conducting at least one aqueous wash of the peroxyester and decanting the resultant aqueous phase from the resultant purified peroxyesterrs.

6. A process according to claim 1 wherein said recovery in the absence of an organic solvent comprises washing the peroxyester from step (b) with water, separating the resultant washed peroxyester with aqueous potassium or sodium hydroxyl and decanting the resultant aqueous phase from the resultant washed peroxyester.

7. A process for the preparation of a peroxyester said process comprising conducting the following sequential steps:

(a) reacting an hydroxyhydroperoxide with a base in the absence of an organic solvent, and with a molar ratio $R_a$ of the base to the hydroperoxide of between 0.9 and 1.3, to obtain a salt of the hydroxyhydroperoxide, (b) on completion of step (a) reacting resultant salt of hydroxyhydroperoxide with an acid chloride to form a peroxyester, wherein the mol ratio $R_b$ of the hydroxyhydroperoxide corresponding to the salt to the acid halide is between 0.5 and 1.5, (c) recovering said peroxyester from step (b) so as to produce a final product, said recovery being conducted in the absence of an organic solvent, and wherein the hydroxyhydroperoxide is a hydroxy(tertiary-alkyl) hydroperoxide in which the hydroxyl group is situated in the 3 position with respect to the hydroperoxy group.

8. A process according to claim 1, wherein the hydroxyhydroperoxide corresponds to the following formula:

$$HO-C(R_3)(R_4)-CH_2-C(R_1)(R_2)-OOH$$

in which:

$R_1$ and $R_2$ are, independently of one another, an alkyl having from 1 to 4 carbon atoms;

$R_3$ and $R_4$ are, independently of one another, a hydrogen or an alkyl having from 1 to 4 carbon atoms;

$R_1$ and $R_3$ can be connected to one another via an alkylene bridge having 3 carbon atoms, this bridge optionally being substituted by an alkyl having from 1 to 4 carbon atoms; and $R_3$ can additionally be a $-CH_2-C(R_1)(R_2)-OOH$ group.

9. A process according to claim 8, wherein the hydroxyl (tertiary-alkyl)hydroperoxide is chosen from the group consisting of 3-hydroxy-1,1-dimethylpropyl, 3-hydroxy-1,1-dimethylbutyl, 1-ethyl-3-hydroxy-1-methylpentyl, 1,1-diethyl-3-hydroxybutyl and 5-hydroxy-1,3,3-trimethylcyclohexyl hydroperoxides.

10. A process according to claim 1, wherein it is carried out in the absence of a phase transfer catalyst.

11. A process according to claim 1, wherein the base is KOH.

12. A process according to claim 1, wherein said resultant salt is reacted with said acid anhydride in the absence of an organic solvent to form a peroxyester, said anhydride being chosen from anhydrides of 2-methoxypropionic, isobutyric, tert-butyric, pivalic, 2,2-dimethylbutyric, 2-ethylbutyric, hexanoic, neohexanoic, benzoic, heptanoic, neoheptanoic, 2-ethylhexanoic, octanoic, neooctanoic, 2-phenoxypropanoic, 2-phenylpropanoic, nonanoic, isononanoic, neononanoic, 2-methyl-2-phenyl-propionic, 2-phenylbutyric, decanoic, neodecanoic, dodecanoic, 2-butyloctanoic, neododecanoic, undecanoic, neotridecanoic, methacrylic, methylcrotonic and 2-methyl-2-butenoic acids.

13. A process according to claim 1, wherein the reaction is carried out between a hydroxyhydroperoxide salt and an acid halide.

14. A process according to claim 13, wherein the acid halide corresponds to the formula R'COX, in which:

R' corresponds to one of the following formulae:

$$R_5R_6R_7C- \text{ and } R_9CH=CR_8-$$

in which:

$R_5$ is a hydrogen or an alkyl having from 1 to 8 carbon atoms;

$R_6$ is an alkyl having from 1 to 8 carbon atoms;

$R_7$ is an alkyl having from 1 to 8 carbon atoms, an alkenyl having from 2 to 8 carbon atoms, an aryl having from 6 to 10 carbon atoms, an alkoxy having from 1 to 6 carbon atoms or an aryloxy having from 6 to 10 carbon atoms;

$R_8$ and $R_9$ are, independently of one another, an alkyl having from 1 to 4 carbon atoms; and X is a halogen.

15. A process according to claim 14, characterized in that the halide is chosen from 2-methoxypropionyl, isobutyroyl, tert-butyroyl, pivaloyl, 2,2-dimethylbutyroyl, 2-ethylbutyroyl, hexanoyl, neohexanoyl, benzoyl, heptanoyl, neoheptanoyl, 2-ethylhexanoyl, octanoyl, neooctanoyl, 2-phenoxypropanoyl, 2-phenylpropanoyl, nonanoyl, isononanoyl, neononanoyl, 2-methyl-2-phenylpropionyl, 2-phenylbutyroyl, decanoyl, neodecanoyl, dodecanoyl, 2-butyloctanoyl, neododecanoyl, undecanoyl, neotridecanoyl, methacryloyl, methylcrotonoyl and 2-methyl-2-butenoyl halides.

16. A process according to claim 15, wherein the acid halide is an acid chloride.

17. A process according to claim 16, wherein the acid halide is neodecanoyl chloride.

18. A process according to claim 1, wherein the ratio $R_b$ is between 0.9 and 1.2.

19. A process according to claim 1, wherein the hydroxyhydroperoxide is 3-hydroxy-1,1-dimethylbutyl hydroperoxide and the acid halide is neodecanoyl chloride.

20. A process according to claim 1, further comprising forming an aqueous emulsion comprising at least one peroxyester obtained by the process of claim 1.

21. A process according to claim 1, further comprising conducting a polymerization process employing a radical initiator comprising at least one peroxyester obtained by the process of claim 1.

22. A process according to claim 18, wherein the mol ratio $R_b$ is between 1.00 and 1.16.

* * * * *